United States Patent
Toyoda et al.

[19]

[11] Patent Number: 5,916,207
[45] Date of Patent: Jun. 29, 1999

[54] DISPOSABLE DIAPERS WITH FASTENING TAPES BECOMING ELASTIC DURING USE

[75] Inventors: Harumitsu Toyoda; Fumiaki Kikuchi, both of Haga-gun, Japan

[73] Assignee: KAO Corporation, Tokyo, Japan

[21] Appl. No.: 08/849,881

[22] PCT Filed: Nov. 7, 1996

[86] PCT No.: PCT/JP96/03259

§ 371 Date: Jun. 18, 1997

§ 102(e) Date: Jun. 18, 1997

[87] PCT Pub. No.: WO97/17927

PCT Pub. Date: May 22, 1997

[30] Foreign Application Priority Data

Nov. 14, 1995 [JP] Japan .................................. 7-295837

[51] Int. Cl.⁶ .................................................. A61F 13/15
[52] U.S. Cl. ..................... 604/391; 604/389; 604/386; 428/343; 428/100; 24/442
[58] Field of Search ................. 604/373, 385.2, 604/386, 387, 389, 390, 391; 428/343, 100; 24/442

[56] References Cited

U.S. PATENT DOCUMENTS

| | | | |
|---|---|---|---|
| 3,750,669 | 8/1973 | DeLuca | 604/390 |
| 3,800,796 | 4/1974 | Jacob | 604/373 |
| 4,209,016 | 6/1980 | Schaar | 604/390 |
| 4,787,897 | 11/1988 | Torimae et al. | 604/389 |
| 4,795,456 | 1/1989 | Borgers et al. | 604/389 |
| 4,973,326 | 11/1990 | Wood et al. | 604/391 |
| 5,057,097 | 10/1991 | Gesp | 604/389 |
| 5,106,383 | 4/1992 | Mulder et al. | 604/390 |
| 5,264,281 | 11/1993 | Arakawa et al. | 604/389 |
| 5,429,856 | 7/1995 | Krueger et al. | 604/389 |
| 5,605,735 | 2/1997 | Zehner et al. | 604/389 |
| 5,779,691 | 7/1998 | Schmitt | 604/389 |

FOREIGN PATENT DOCUMENTS

| | | |
|---|---|---|
| 0191355 | 8/1986 | European Pat. Off. . |
| 0249073 | 12/1987 | European Pat. Off. . |
| 0487758 | 6/1992 | European Pat. Off. . |
| 0704196 | 4/1996 | European Pat. Off. . |
| A-5-7161101 | 10/1982 | Japan . |
| A-1-168901 | 7/1989 | Japan . |
| A-3-47884 | 2/1991 | Japan . |
| 410817 | 3/1992 | Japan . |
| U-4-50025 | 4/1992 | Japan . |
| A-6-502355 | 3/1994 | Japan . |
| 7231913 | 5/1995 | Japan . |
| 761351 | 7/1995 | Japan . |

*Primary Examiner*—Mark O. Polutta
*Attorney, Agent, or Firm*—Birch, Stewart, Kolasch & Birch, LLP

[57] ABSTRACT

A disposable diaper includes a liquid permeable topsheet, a liquid impermeable backsheet, and an absorbent member interposed between the topsheet and backsheet. When worn, the diaper forms a front waist body portion, a rear waist body portion, and a crotch portion. The rear waist body portion has at each side, a fastening tape which is designed to reveal elasticity on being pulled in the longitudinal direction of the fastening tape.

8 Claims, 2 Drawing Sheets

DISPOSABLE DIAPERS WITH FASTENING TAPES BECOMING ELASTIC DURING USE

TECHNICAL FIELD

This invention relates to a disposable diaper and more particularly to a disposable diaper having a novel fastening tape efficient in productivity.

BACKGROUND ART

Disposable diapers often have a means for gathering up at the waist to improve a fit of the waist opening portion while worn, such as fastening tapes made of an elastic member (see Japanese Patent Publication No. 7-61351 and Japanese Utility Model Publication No. 4-10817) or an elastic member that is provided at the rear waist portion.

In order to gather at the waist by the above-mentioned conventional means, an elastic member having elasticity must be fixed at a prescribed position of a diaper with a necessary step of stretching the elastic member in a series of a production system. Therefore the elastic member cannot be transported, fixed, and assembled into a diaper in the same manner as other members, which has caused poor productivity. Further, a complicated processing step is involved which increases cost.

Japanese Patent Laid-Open No. 7-231913 discloses a porous sheet in which areas having no elasticity but moisture permeability alternate with areas having no moisture permeability but elasticity. The publication further discloses the use of the porous sheet in absorbent articles, for example, as a back sheet of a disposable diaper. However, the publication neither discloses nor suggests use of the porous sheet as a fastening tape for diapers.

DISCLOSURE OF THE INVENTION

An object of the present invention is to provide a disposable diaper that can be gathered at the waist without reducing productivity or involving a complicated processing step.

As a result of extensive study, it has been found that the above object is accomplished by designing a fastening tape so as to reveal elasticity on pulling to its longitudinal direction.

The present invention has been completed based on this finding. The invention provides a disposable diaper which comprises a liquid permeable topsheet, a liquid impermeable back sheet, and an absorbent member interposed between the topsheet and the back sheet, and has a structure to form, when worn, a front waist body portion, a rear waist body portion and a crotch portion, the rear waist body portion having at each side thereof a fastening tape for fastening the diaper, wherein the fastening tape is designed to reveal elasticity on being pulled in the longitudinal direction thereof.

The invention provides the above-described disposable diaper, wherein the fastening tape has a tip portion having a first fastening means provided on one surface side thereof, a central portion which reveals elasticity on being pulled in the longitudinal direction of the tape, and a fixed portion which is fixed at the rear waist body portion, and the back sheet is provided with a second fastening means on the surface side thereof so that the diaper may be removably fastened by binding the first fastening means and the second fastening means.

The invention provides the above-described disposable diaper, wherein either one of the first fastening means and the second fastening means is made of a male member of a mechanical fastener and the other is made of a female member of the mechanical fastener or nonwoven fabric engageable with the male member.

The invention provides the above-described disposable diaper, wherein the central portion of the fastening tape has (a) a plastic deformable area and (b) a stretchable area, each being formed on at least one surface side of said central portion and extending in the longitudinal direction of the tape.

The invention provides the above-described disposable diaper, wherein the stretchable area (b) is provided on the plastic deformable area (a) in a line, a band or a spiral form.

The invention provides the above-described disposable diaper, wherein a plurality of the stretchable areas (b) alternate with the plastic deformable areas (a) in the width direction of the tape.

The invention provides the above-described disposable diaper, wherein the plastic deformable area (a) and the stretchable area (b) have an area ratio, (a)/(b), of ⅖ to 8/2.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention will become more fully understood from the detailed description given hereinbelow and the accompanying drawings which are given by way of illustration only, and thus are not limitative of the present invention, and wherein:

BEST MODE FOR CARRYING OUT THE INVENTION

Figure 1:
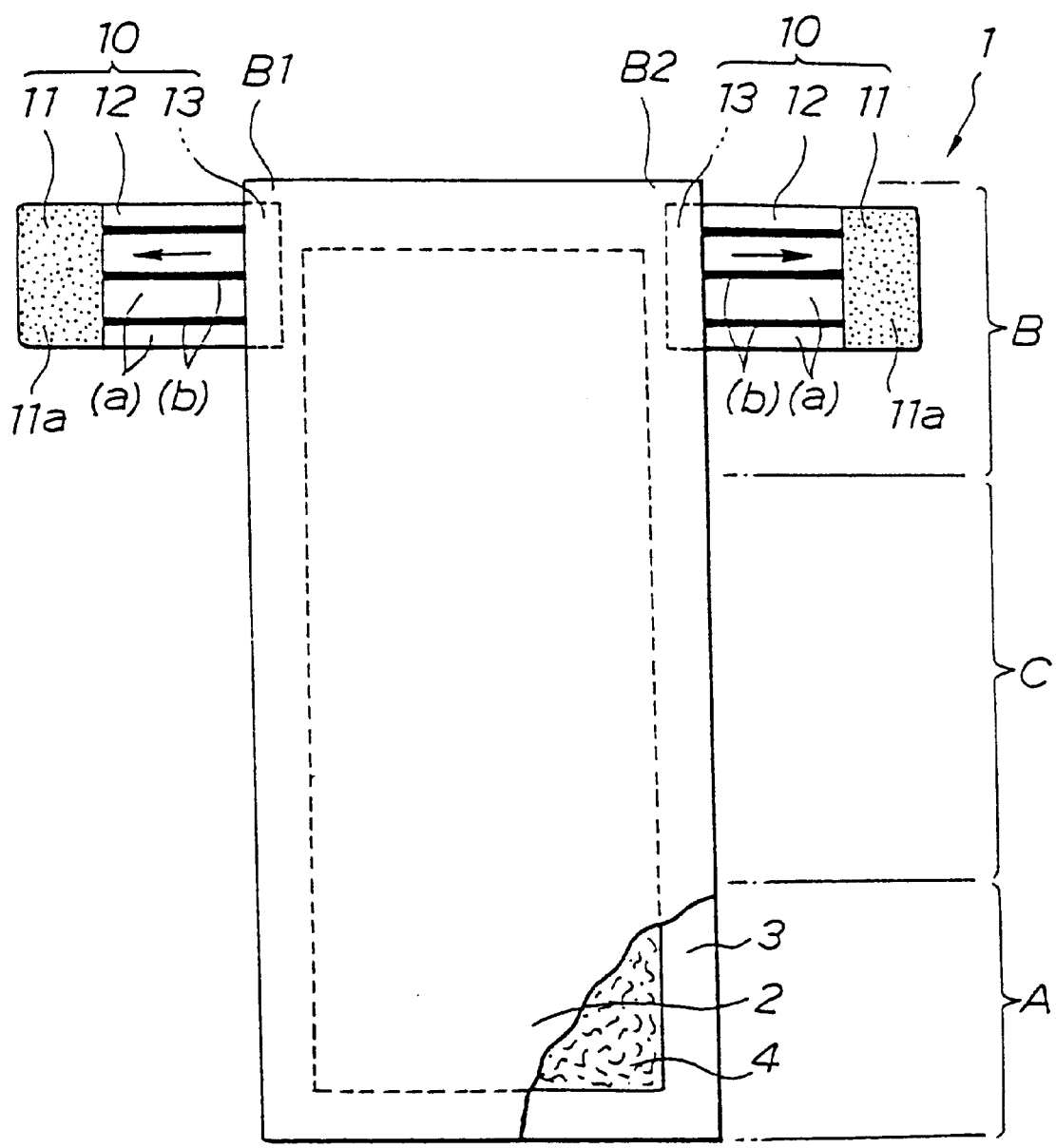
FIG. 1 is a plane view of an example of the disposable diaper of the invention in its unfolded condition.
Figure 2:
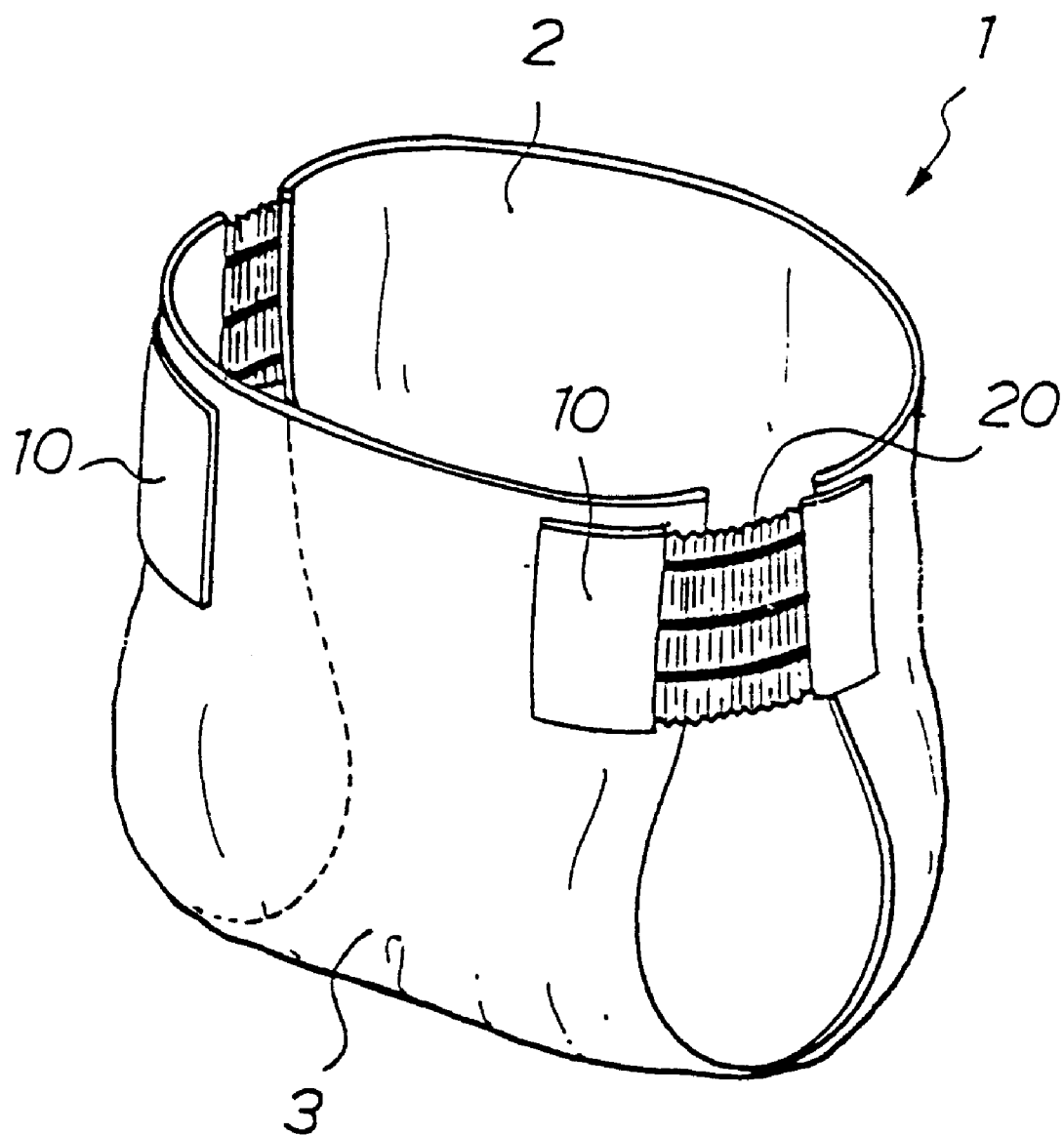
FIG. 2 is a perspective view of the disposable diaper of FIG. 1 in its shaped condition.

The disposable diaper of the invention is explained with reference to one embodiment by referring to the accompanying drawings. FIG. 1 is a plane view of one embodiment of the disposable diaper of the invention in its unshaped condition. FIG. 2 is a perspective view of the disposable diaper of FIG. 1 in its shaped condition.

As shown in FIGS. 1 and 2 the disposable diaper 1 according to this embodiment comprises a liquid permeable topsheet 2, a liquid impermeable back sheet 3, and an absorbent member 4 interposed therebetween. The disposable diaper has a structure comprising portions A, B and C to form, when worn, a front waist portion, a rear waist portion and a crotch portion. The portion B corresponding to the rear waist portion has a fastening tape 10 at both side edges thereof B1 and B2. Such a structure is the same as in conventionally known disposable diapers.

The topsheet 2, back sheet 3, and absorbent member 4 each has a rectangular shape to form the disposable diaper 1 in a rectangular shape as well.

The topsheet 2, back sheet 3 and absorbent member 4 can be made of any material conventionally employed in disposable diapers with no particular limitation. When a mechanical fastener (also called a planar fastener or a hook-loop tape) is used as a first fastening means as hereinafter described, the back sheet 3 can be made of hydrophobic nonwoven fabric. It should be understood, however, that the first fastening means is not limited to the mechanical fastener.

In the disposable diaper 1, the fastening tape 10 is designed to reveal elasticity upon being pulled in the longitudinal direction thereof.

The language "designed to reveal elasticity upon being pulled in the longitudinal direction thereof" as used herein is intended to mean that the fastening tape has the structure which shows no elasticity before use but reveals elasticity when stretched by pulling in the longitudinal direction on use. More specifically, the fastening tape is formed of, for example, a striped sheet or the like hereinafter described.

As shown in FIG. 1, the fastening tape 10 has on one surface side thereof (the surface side contacting with backsheet) a tip portion 11 on which a male member (hooks) of "Magic Tape" (a registered trade name of a mechanical fastener) is attached as a first fastening means 11a, a central portion 12 which reveals elasticity on being pulled in its longitudinal direction, and a fixed portion 13 at which the tape is fixed to the rear waist portion B of the diaper. The back sheet 3 is made of hydrophobic nonwoven fabric, and the nonwoven fabric itself serves as a second fastening means. The diaper is removably fitted to a wearer by binding the first fastening means 11a and the second fastening means, i.e., the nonwoven fabric forming the back sheet 3.

In the disposable diaper 1 according to this embodiment, the first fastening means is formed of a male member of a mechanical fastener, and the second fastening means is formed of nonwoven fabric engageable with the male member.

As shown in FIG. 1, the fastening tape 10 is formed so as to give (a) a plastic deformable area and (b) a stretchable area on at least one side of the central portion 12, each extending in the longitudinal direction of the tape substantially in parallel with each other. There may be a single or a plurality of the stretchable areas (b). In the latter case, the plastic deformable areas (a) and the stretchable areas (b) alternate with each other in the tape width direction to form stripes. For causing stable elastic property of the fastening tape, the number of the stretchable areas (b) is preferably 1 to 10. Because the tip portion 11 has a male member of a mechanical fastener attached to one surface side thereof, and the fixed portion 13 is fixed to the back sheet 3 via an adhesive, these portions are designed not to reveal elasticity. In other words, only the central portion is designed to reveal elasticity.

The fastening tape 10 of the present invention can be formed of a sheet having on at least one side thereof the above-mentioned plastic deformable area (a) and stretchable area (b). Such a sheet includes a sheet made up of a material forming the plastic deformable area (a) having provided thereon a material forming the stretchable area (b) in the form of a line, a spiral, etc.

The area ratio of the plastic deformable area (a) to the stretchable area (b), (a):(b), is preferably 2:8 to 8:2, more preferably 4:6 to 6:4. The weight ratio of the material forming the plastic deformable area (a) to the material forming the stretchable area (b), (a):(b), is preferably 2:8 to 8:2.

Where the stretchable area is formed in a line, the line width is preferably 1 to 10 mm.

The width of the fastening tape 10 is arbitrary according to the size of the diaper and is preferably 15 to 50 mm.

Materials forming the plastic deformable area (a) and the stretchable area (b) are explained below.

The material forming the plastic deformable area (a) is not restricted, when said material has the plastic deformable property. As said material, polyolefin resins such as polyethylene resin, polypropylene resin, ethylene propylene copolymer, and the like can be included. The preferable polyolefin resins are high-density polyethylene, low-density polyethylene, and linear low-density polyethylene (LLDPE). LLDPE having a density of 0.910 to 0.940 g/cm$^3$ and a melt flow rate (MFR) of 0.1 to 5 g/10 min are particularly preferred. The plastic deformable material capable of forming a moisture permeable sheet, which is disclosed in Japanese Patent Laid-Open No. 7-231913, can be preferably used. For example, the following compositions (1) to (3) are preferably used.

Composition (1): A composition comprising 100 parts by weight of a polyolefin resin, 50 to 400 parts by weight of a filler, and 0.1 to 20 parts by weight of a softener.

Composition (2): A composition obtained by melt-kneading 65 to 90 parts by weight of a crystalline polyolefin and 10 to 35 parts by weight of a compound which has miscibility with and solubility in the crystalline polyolefin at temperatures at and above the melting point of the crystalline polyolefin but undergoes phase separation from the crystalline polyolefin at temperatures below the melting point of the crystalline polyolefin.

Composition (3): A composition obtained by melt-kneading 100 parts by weight of a polyolefin resin and 10 to 100 parts by weight of a thermoplastic resin which is incompatible with the polyolefin resin.

The stretchable area (b) constituting the fastening tape of the invention is an area for imparting elasticity to the fastening tape. The stretchable area (b), when stretched, preferably has such elasticity that the residual strain after 50% stretch and relief of the tension is not more than 20%.

The material forming the stretchable area (b) preferably includes thermoplastic elastomers. Examples of suitable thermoplastic elastomers are styrene elastomers, olefin elastomers, polybutadiene elastomers, polyester elastomers, polyamide elastomers, urethane elastomers, vinyl chloride elastomers, fluorine-containing elastomers, ionomer resins, silicone resins, and mixtures thereof. Styrene elastomers and olefin elastomers are particularly preferred.

In order to prevent the stretchable area (b) from temporarily shrinking after being stretched together with the plastic deformable area (a), a composition comprising the thermoplastic elastomer and a polyolefin resin as an additional thermoplastic resin is preferably used as a material for forming the stretchable area (b). In this case, styrene elastomers or olefin elastomers are preferably used for their compatibility with the polyolefin resin.

The polyolefin resin to be combined with the thermoplastic elastomer can be selected from the same polyolefin resins as used as a material for forming the plastic deformable area (a).

A preferred weight ratio of the styrene elastomer or olefin elastomer to the polyolefin resin is 80/20 to 20/80, particularly 70/30 to 30/70.

The styrene elastomer includes "Kraton" and "Califlex" both produced by Shell Chemical Co., Ltd., and "TUF-PRENE" and "SOLPRENE" both produced by Asahi Chemical Industry Co., Ltd. The olefin elastomer includes "Milastomer" produced by Mitsui Petrochemical Industries, Ltd. and "Sumitomo TPE" produced by Sumitomo Chemical Co., Ltd.

When a styrene elastomer composition is used as a material for forming the stretchable area (b), the most preferred composition comprises (i) 0.3 to 0.7 part by weight of a styrene elastomer which is an aromatic vinyl compound-conjugated diene block copolymer having the aromatic vinyl compound content of 10 to 40% by weight with the conjugated diene moiety thereof being hydrogenated, (ii) 0.2 to 0.6 part by weight of a polyolefin resin, and (iii) 0.05 to 0.3 part by weight of a resin having a melting point or a softening point of not lower than 80° C. and an average molecular weight of 400 to 2000.

The component (i) is a thermoplastic elastomer of aromatic hydrocarbon polymer type which comprises at least one polymer block of an aromatic vinyl compound and at least one hydrogenated conjugated diene polymer block.

While the method for obtaining the derivative in which the diene moiety is hydrogenated is not limited, it is preferable for imparting elasticity to the stretchable area (b) that at least 80% of the conjugated diene block(s) be hydrogenated.

The aromatic vinyl compound is a styrene type monovinyl-substituted aromatic hydrocarbon, preferably styrene. α-methylstyrene, etc. are also useful.

The conjugated diene is preferably butadiene, isoprene or a mixture thereof.

The weight ratio of the aromatic vinyl compound polymer block A to the conjugated diene polymer block B is preferably 10/90 to 40/60. The total number average molecular weight of the polymer block A and the polymer block B is preferably more than 20000, still preferably 30000 to 250000, particularly preferably 40000 to 200000, as measured by gel-permeation chromatography (GPC).

The olefin resin as component (ii) includes olefin thermoplastic resins comprising homo- or copolymers of α-olefins, such as ethylene, propylene, butylene, etc. Resins generally used in thermoplastic molding are used. Preferred of them are specific polyethylene or polypropylene used for the injection or extrusion molding. For use in which softness is required as in diapers, low-density polyethylene is suitable. Linear low-density polyethylene (LLDPE) is particularly suitable.

The resin as component (iii) is preferably a resin having a melting point or softening point of not lower than 80° C., still preferably not lower than 100° C., and a number average molecular weight of 400 to 2000, preferably 600 to 1500. Such a resin includes hydrogenated terpene resins and alicyclic hydrogenated resins.

Typical examples of such a resin include "CLEARON" produced by Yasuhara Yushi K. K. and "ARKON" produced by Arakawa Kagaku Kogyo K. K.

The sheet for forming the fastening tape can easily be obtained by extruding the material for forming the plastic deformable area (a) to obtain a moisture permeable sheet, and extrusion laminating the material for forming the stretchable area (b) onto the moisture permeable sheet in places, e.g., in the form of line(s), band(s) or spiral(s).

The disposable diaper 1 according to this embodiment can be put on a wearer by stretching the fastening tape 10 by pulling to its longitudinal direction (the direction indicated by the arrow in FIG. 1) and applying the mechanical fastener 11 (the first fastening means) to the back sheet 3 to fasten the diaper as shown in FIG. 2.

Because the disposable diaper of the invention has the above-mentioned fastening tape 10, there is no need in the production of the disposable diaper to attach an elastic member, under stretched condition, to a prescribed position of a diaper, thus providing excellent productivity. The fastening tape 10 has no elasticity before use but, when it is put on a wearer (e.g.,baby), it reveals elasticity upon user's (e.g., mother's) pulling the tape to stretch the plastic deformable area (a). As illustrated in FIG. 2, the fastening tape 10 revealing elasticity forms gathers 20 at the waist so that the waist portion has an improved fit through the elasticity of the waist gathers 20.

The disposable diaper of the invention is by no means limited to the above-described embodiment. For example, the sheet for forming the fastening tape may be a striped sheet obtained by co-extrusion of the material for forming the plastic deformable area (a) and the material for forming the stretchable area (b) in such a manner that plastic deformable areas (a) and stretchable areas (b) alternative with each other.

Further, the mechanical fastener as the first fastening means may be replaced with an adhesive. In this case, the material for forming the back sheet is not limited to nonwoven fabric. While any material in general use may be employable as a back sheet-forming material, it is preferred in this case to use a sheet material to which the adhesive tape can be removably stuck, or to provide a generally known landing tape on the surface of the back sheet. In these cases, the sheet itself to which an adhesive tape can be removably stuck or the landing tape serves as the second fastening means.

On the other hand, a certain shape of female member of the mechanical fastener or nonwoven fabric may be attached at a prescribed position of the surface of the back sheet to provide a second fastening means.

Furthermore, a female member of the mechanical fastener or nonwoven fabric may be attached to the tip portion of the fastening tape to provide a first fastening means, while a male member may be attached to the back sheet as a second fastening means.

The fastening tape can be designed to reveal elasticity over the entire area thereof, and a fastening means may be provided at portions other than the tip portion.

Unlike the embodiment shown in FIGS. 1 and 2, a tip portion, a central portion, and a fixed portion of the fastening tape may be prepared separately and joined together at the respective ends to form a fastening tape as a whole.

The shape of the disposable diaper is not limited to a rectangle as particularly referred to above. For example, the diaper may have the portion corresponding to the crotch portion in use narrowed to have a sandglass-like shape. An elastic member may be provided at the portions corresponding to the leg opening portions.

The central portion of the fastening tape does not need to have stretchability over the entire area thereof as long as at least part of it is stretchable to reveal elasticity.

INDUSTRIAL APPLICABILITY

The disposable diaper of the invention is designed to reveal elasticity at the fastening tape thereof through put-on operations of a user without being accompanied by reduction in productivity or involvement of complicated processing steps. By virtue of the thus revealed elasticity, the gathers can be formed at the waist portion of the diaper where no gathers had existed before use.

We claim:

1. A disposable diaper comprising:

a liquid permeable topsheet;

a liquid impermeable backsheet;

an absorbent member interposed between said topsheet and said backsheet; said topsheet, said backsheet, and said absorbent member forming a front waist body portion, a rear waist body portion and a crotch portion when said diaper is worn; and a tape fastener connecting the front waist body portion to said rear waist body portion, said tape fastener including a tip portion with a first fastening means provided on one surface side thereof, said tape fastener including a central portion and a fixed portion, said central portion being designed to reveal elasticity when pulled in a longitudinal direction thereof, said fixed portion being secured to said waist body portion, said back sheet being provided with a second fastening means, said first fastening means being removably connected to said second fastening means, said central portion of said tape fastener further including a plastic deformable area and a stretchable area forming a single planar sheet and extending in a longitudinal direction of said tape fastener, said plastic deformable area and said stretchable area being separated from each other in a tape width direction, said plastic deformable area forming gathers when said diaper is worn where said first fastening means is removably connected to said second fastening means, whereby said tape fastener substantially improves a fit of said front and said rear waist body portions on a user while substantially increasing manufacturing efficiency of said diaper.

2. The disposable diaper according to claim 1 wherein either one of said first fastening means and said second fastening means is made of a male member of a mechanical fastener and the other is made of a female member of the mechanical fastener or nonwoven fabric engageable with said male member.

3. The disposable diaper according to claim 1 wherein said stretchable area is provided in a line, a band or a spiral form.

4. The disposable diaper according to claim 1 wherein a plurality of stretchable areas alternate with a plurality of plastic deformable areas in the width direction of the fastening tape.

5. The disposable diaper according to claim 1 wherein said plastic deformable area and said stretchable area have an area ratio of $2/8$ to $8/2$.

6. The disposable diaper according to claim 1 wherein the plastic deformable area comprises polyolefin resin.

7. The disposable diaper according to claim 1 wherein the stretchable area comprises styrene elastomer or olefin elastomer.

8. The disposable diaper according to claim 7, wherein the stretchable area further comprises polyolefin resin.

* * * * *